(12) United States Patent
Horstman et al.

(10) Patent No.: US 8,808,680 B2
(45) Date of Patent: Aug. 19, 2014

(54) IONOMERIC SILICONE THERMOPLASTIC ELASTOMERS

(71) Applicant: Dow Corning Corporation, Midland, MI (US)

(72) Inventors: John Bernard Horstman, Midland, MI (US); Randall Gene Schmidt, Midland, MI (US); Steven Swier, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/668,456

(22) Filed: Nov. 5, 2012

(65) Prior Publication Data

US 2014/0121320 A1    May 1, 2014

Related U.S. Application Data

(62) Division of application No. 12/809,610, filed as application No. PCT/US2008/087327 on Dec. 18, 2008, now Pat. No. 8,329,156.

(60) Provisional application No. 61/015,697, filed on Dec. 21, 2007.

(51) Int. Cl.
| | |
|---|---|
| *A61K 31/765* | (2006.01) |
| *C08G 77/14* | (2006.01) |
| *C08L 83/06* | (2006.01) |
| *C09J 5/06* | (2006.01) |
| *A61K 8/893* | (2006.01) |
| *A61Q 19/00* | (2006.01) |

(52) U.S. Cl.
CPC .............. *A61K 8/893* (2013.01); *A61K 31/765* (2013.01); *A61Q 19/00* (2013.01); *C08L 83/06* (2013.01); *C08G 77/14* (2013.01); *C09J 5/06* (2013.01)
USPC ........ 424/78.37; 156/329; 524/588; 525/474; 528/30; 528/39

(58) Field of Classification Search
CPC ... A61K 2800/48; A61K 8/893; A61Q 19/00; C08G 2170/20; C08G 77/14; C08G 77/398; C08L 83/06; C09J 183/06

USPC ........ 424/78.37; 156/329; 524/588; 525/474; 528/30, 39
See application file for complete search history.

(56) References Cited

U.S. PATENT DOCUMENTS

| | | | |
|---|---|---|---|
| 2,676,182 A | 4/1954 | Daudt et al. |
| 3,047,528 A | 7/1962 | Bluestein |
| 4,495,340 A | 1/1985 | Blizzard et al. |
| 4,840,693 A | 6/1989 | Suzuki et al. |
| 5,194,251 A | 3/1993 | Halloran et al. |
| 5,596,061 A | 1/1997 | Berger et al. |
| 5,976,517 A | 11/1999 | Dubief et al. |
| 5,990,334 A | 11/1999 | Hierstetter et al. |
| 6,124,490 A | 9/2000 | Gormley et al. |
| 6,749,943 B1 | 6/2004 | Tangen et al. |
| 2008/0293878 A1 | 11/2008 | Funk et al. |

FOREIGN PATENT DOCUMENTS

| | | | | |
|---|---|---|---|---|
| DE | WO 2007/063046 | * | 6/2007 | ............. C08G 77/58 |
| JP | 05320234 | | 12/1993 | |
| WO | 2007063046 | | 6/2007 | |

OTHER PUBLICATIONS

Gornowicz et al., Polymeric Material Science and Engineering, vol. 59, Jan 1, 1988, pp. 1009-1013.
Blagodatskikh et al., Polmer Science, Interperiodica, vol. 38, No. 11, Nov. 11, 1996, pp. 1239-1243.
Walker, Handbook of Adhesive Technology. Second Edition, Chapter 10, 1993 p. 1-17.
Jiri George Drobny: "Applications of Thermoplastice Elastomers" In: "Handbook of Thermoplastice Elastomers", Jan. 1, 2007, pp. 281-315.
"Silicones", Apr. 15, 2003, Encyclopedia of Polymer Science and Technology, Wiley, US, pp. 765-841.

\* cited by examiner

*Primary Examiner* — Anoop Singh
*Assistant Examiner* — Anna Falkowitz
(74) *Attorney, Agent, or Firm* — Catherine U. Brown

(57) ABSTRACT

This invention relates to thermoplastic elastomers comprising at least one silicone ionomer. These thermoplastic elastomers may be reprocessed and/or recycled.

12 Claims, 3 Drawing Sheets

IONOMERIC SILICONE THERMOPLASTIC ELASTOMERS

CROSS-REFERENCE TO RELATED APPLICATIONS

This is a U.S. divisional application of U.S. application Ser. No. 12/809,610, which was a national stage filing under 35 U.S.C. §371 of PCT Application No. PCT/US08/87327 filed on 18/DEC/2008, which claimed the benefit of U.S. Provisional Patent Application No. 61/015,697 filed 21/DEC/2007 under 35 U.S.C. §119 (e).

BACKGROUND OF THE INVENTION

This invention relates to thermoplastic elastomers comprising at least one silicone ionomer. Ionomers as defined herein are polymers in which the bulk properties are governed by ionic interactions in discrete regions of the material (i.e., ionic aggregates). These predominantly nonpolar macromolecules contain ionic groups as part of the chain, usually at levels less than 15 mol %. Broad literature exists on organic ionomers. Phase segregation of the ionic groups from the bulk of the polymer results in the formation of a second phase, termed ionomeric aggregates. A combination of the difference in solubility parameter between the ionic and siloxane phase and the strong ionic and coordinate bonding formed accounts for the formation of these aggregates.

According to the Eisenberg-Hird-Moore (EHM) model, the ionomeric aggregates occupy a region of about 6 Å and affect a region of about 30 Å resulting in a state of reduced polymer mobility. The small size of these ionomeric aggregates (less then the wavelength of light) ensures the transparency of these materials. The aggregation of ionic groups, also termed "multiplets", can impart physical crosslinks to the base polymer, greatly modifying the viscoelastic properties of the resulting polymer. In addition, since the crosslinks are physical crosslinks they may be broken up by heating or dissolution and therefore the materials they form may be recycled and/or reformed.

Generally, silicone polymers can form either thermoset or thermoplastic elastomers. With a thermoset elastomer, the silicone polymers are chemically crosslinked. These types of crosslinks are not reversible and therefore thermoset elastomers are not recyclable. Thermoplastic elastomers are polymeric materials which possess both plastic and rubbery properties. Thermoplastic elastomers can be processed using conventional polymer processing methods like extrusion, blow molding, melt spinning, etc. which are challenging for thermosetting systems. They have elastomeric mechanical properties but, unlike conventional thermoset rubbers, they can also be re-processed at elevated temperatures. This re-processability is a major advantage of thermoplastic elastomers over chemically crosslinked rubbers since it allows recycling of fabricated parts and results in a considerable reduction of scrap. With the increased focus on the environment it is very important to develop materials that can be recycled and/or reprocessed when no longer needed.

BRIEF SUMMARY OF THE INVENTION

The present invention is a thermoplastic elastomer comprising at least one silicone ionomer having an average Formula (1) $(X_vR_{3-v}SiO_{1/2})_a(X_wR_{2-w}SiO_{2/2})_b(X_yR_{1-y}SiO_{3/2})_c(SiO_{4/2})_d$, where each R is an independently selected monovalent alkyl group or aryl group, each X is independently selected from a monovalent alkyl group, aryl group and a carboxy functional group having a Formula (2) -G-COOZ, where G is a divalent spacer group having at least 2 spacing atoms, each Z is independently selected from hydrogen or a cation independently selected from alkali metal cations, alkali earth metal cations, transition metal cations, and metal cations, v is 0 to 3, w is 0 to 2, y is 0 to 1, $0 \leq a \leq 0.9$; $0 \leq b < 1$; $0 \leq c \leq 0.9$, $0 \leq d < 0.3$ and $a+b+c+d=1$, provided that on average there is at least 0.002 mole carboxy functional groups per silicon atom and at least 10 mole percent of the Z groups of the carboxy functional group are an independently selected cation.

The inventors have determined that certain silicone ionomers can form physical crosslinks which increase viscosity and can impart elastomeric behavior. Unlike materials having chemical crosslinks, materials comprising silicone ionomers may be recycled and/or reprocessed when no longer needed. An object of the present invention is to describe thermoplastic elastomers comprising at least one silicone ionomer. Another object of the present invention is to describe a method of sealing or bonding two substrates using the thermoplastic elastomers as a hot melt material comprising at least one silicone ionomer or a blend of silicone ionomers.

DETAILED DESCRIPTION OF THE INVENTION

Figure 1:
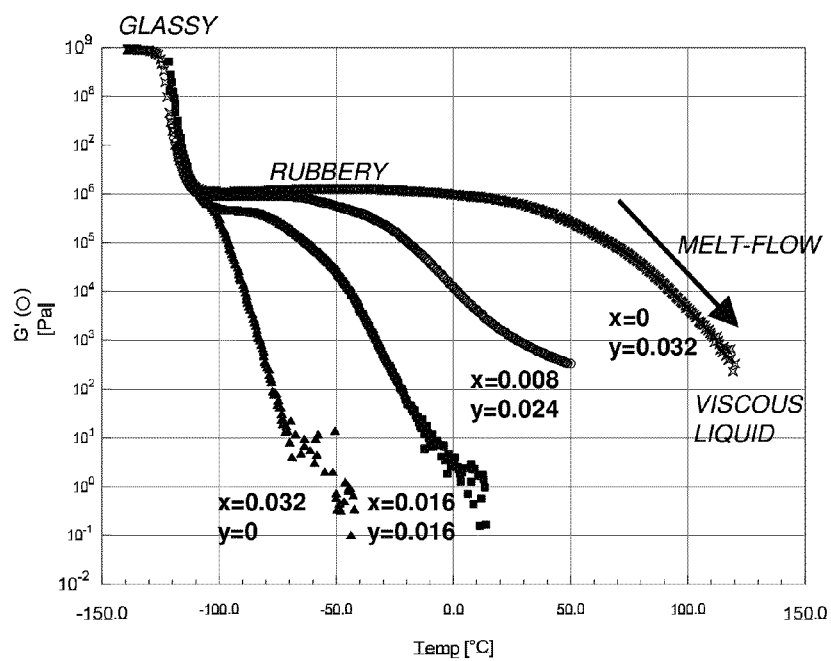
FIG. 1: Storage modulus (G') of polydimethylsiloxanes bearing pendant carboxy acid functional radicals, neutralized with different levels of Lithium counter-ions; x and y refer to the Formula $(Me_3SiO_{1/2})_{0.018}(MeR'SiO_{2/2})_x(MeR''SiO_{2/2})_y(Me_2SiO_{2/2})_{0.95}$ with R'—$(CH_2)_{10}$—COOH and R''—$(CH_2)_{10}$—COO⁻Li⁺ measurements were performed under oscillatory shear using small sinusoidal strain (<5%).

In the present invention, each silicone ionomer which is useful for making a thermoplastic elastomer has an average Formula (1)

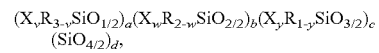

$(X_vR_{3-v}SiO_{1/2})_a(X_wR_{2-w}SiO_{2/2})_b(X_yR_{1-y}SiO_{3/2})_c(SiO_{4/2})_d$, where each R is an independently selected monovalent alkyl group or aryl group, each X is independently selected from a monovalent alkyl group, aryl group and a carboxy functional group having a Formula (2) -G-COOZ, where G is a divalent spacer group having at least 2 spacing atoms, each Z is independently selected from hydrogen or a cation independently selected from alkali metal cations, alkali earth metal cations, transition metal cations, and metal cations, v is 0 to 3, w is 0 to 2, y is 0 to 1, $0 \leq a \leq 0.9$; $0 \leq b < 1$; $0 \leq c \leq 0.9$, $0 \leq d < 0.3$ and $a+b+c+d=1$, provided that on average there is from 0.002 to 0.5 moles carboxy functional groups per silicon atom and at least 10 mole percent of the Z groups of the carboxy functional group are an independently selected cation.

Each R is an independently selected monovalent alkyl group or aryl group. Alternatively, each R is an independently selected alkyl group having 1 to 10 carbon atoms or an aryl group having 6 to 20 carbon atoms. Alternatively, each R is an independently selected methyl or phenyl group. Alternatively, each R is methyl. Examples of useful alkyl groups include methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl and cycloheptyl radicals and methylcyclohexyl radicals Examples of aryl groups include phenyl, naphthyl; o-, m- and p-tolyl, xylyl, ethylphenyl, and benzyl.

In Formula (1), subscript v is 0 to 3, w is 0 to 2, and y is 0 to 1. Further, $0 \leq a \leq 0.9$, alternatively $0 < a \leq 0.7$, alternatively $0 < a \leq 0.5$; $0 \leq b < 1$; alternatively $0.5 \leq b < 1$, alternatively $0.7 \leq b < 1$; $0 \leq c \leq 0.9$, alternatively $0 \leq c \leq 0.5$, alternatively $0 \leq c \leq 0.3$; $0 \leq d \leq 0.3$; alternatively $0 \leq d \leq 0.2$, alternatively $0 \leq d \leq 0.1$, and $a+b+c+d=1$. A person skilled in the art would know that the siloxane units in Formula 1 such as $(X_v R_{3-v} SiO_{1/2})$ are often referred to as a M unit, $(X_w R_{2-w} SiO_{2/2})$ are often referred to as a D unit, $(X_y R_{1-y} SiO_{3/2})$ are often referred to as a T unit, and $(SiO_{4/2})_d$, are often referred to as a Q unit.

Each X group of Formula (2) is independently selected from a monovalent alkyl group, aryl group and a carboxy functional group having the Formula (2) -G-COOZ. With respect to Formula (2), each G is a divalent spacing group having at least 2 spacing atoms, alternatively G is a divalent hydrocarbon group having at least 2 carbon atoms or a divalent hydrocarbonoxy group having at least 2 carbon atoms. Alternatively, G is an alkylene group having 2 to 20 carbon atoms. The divalent hydrocarbon group can be illustrated by alkylene groups selected from $-(CHR^2)_s-$ where s has a value of 2 to 20 and $R^2$ is hydrogen or a group defined by R above, such as $-CH_2CH_2-$, $-CH_2CH(CH_3)-$, $-CH_2CH(CH_3)CH_2-$, $-CH_2CH_2CH(CH_2CH_3)CH_2CH_2CH_2-$. The divalent hydrocarbon group can also be illustrated by arylene groups selected from $-(CH_2)_u C_6H_4-$, $-CH_2CH(CH_3)(CH_2)_u C_6H_4-$, and $-(CH_2)_t C_6H_4(CH_2)_u-$ where t has a value of 1 to 20 and u has a value of 0 to 10. The divalent hydrocarbonoxy group can be illustrated by $-OCH(R)(CH_2)_t-$ and $-OCH(CH_3)(CH_2)_t-$ where R and t is as described above.

With respect to Formula (2), each Z is hydrogen or a cation independently selected from alkali metals, alkali earth metals, transition metals and metals. Alternatively, each cation is independently selected from Li, Na, K, Cs, Mg, Ca, Ba, Zn, Cu, Ni, Ga, Al, Mn, and Cr. Alternatively, each cation is independently selected from Li, Na, K, Zn, Ni, Al, Mn, Mg. Alternatively, each cation is independently selected from Li, Na, K, Zn, Al, Mg. One skilled in the art would understand that a cation derived from a certain metal can have different valences depending on the number of associated ligands. For example, $Mn^{2+}$ and $Mn^{3+}$ neutralized carboxylic acid functional siloxane ionomers can be prepared depending on the manganese neutralization agent used.

Generally, on average there are from 0.002 to 0.5 mole carboxy functional groups per silicon atom. Alternatively, on average there are from 0.01 to 0.4 mole carboxy functional groups per silicon atom. Alternatively, on average there are 0.02 to 0.2 mole carboxy functional groups per silicon atom.

Further, at least 10 mole percent of the Z groups of the carboxy functional group are an independently selected cation. Alternatively, at least 50 mole percent of the Z groups of the carboxy functional group are an independently selected cation. Alternatively, at least 75 mole percent of the Z groups of the carboxy functional group are an independently selected cation. Alternatively, 100 mole percent of the Z groups of the carboxy functional group are an independently selected cation. The carboxy functional group may be present in any of the M, D or T siloxane units described by subscripts a, b, and c. Alternatively, the carboxy functional group may be present in the M and D siloxane units described by subscripts a and b.

The degree of polymerization (dp) of the silicone ionomer can vary depending on the desired properties. Alternatively, the dp of the silicone ionomers can be from 10 to 10,000; alternatively 20 to 5,000; alternatively 40 to 5,000.

Another embodiment of the present invention is a thermoplastic elastomer consisting essentially of at least one silicone ionomer as described above.

In addition to the silicone ionomer, it may also be useful, depending on the desired application for the thermoplastic elastomer, to add at least one MQ resin. MQ resins are macromolecular polymers comprised primarily of $R^1_3 SiO_{1/2}$ and $SiO_{4/2}$ units (the M and Q units, respectively) where $R^1$ is a functional or nonfunctional, substituted or unsubstituted monovalent radical. Alternatively, $R^1$ is methyl or phenyl. Those skilled in the art will appreciate that such resins may also include a limited number of $R^1_2 SiO_{2/2}$ and $R^1 SiO_{3/2}$ units, respectively referred to as D and T units. As used herein, the term "MQ resin" means that, on average, no more than about 20 mole percent of the resin molecules are comprised of D and T units. Generally, when an MQ resin is added up to 80 weight parts based on 100 weight parts of the silicone ionomer may be used. Alternatively, from 10 to 70 weight parts based on 100 weight parts of the silicone ionomer may be used. Alternatively, from 30 to 65 weight parts on the same basis may be used.

MQ resins are commercially available or made by known processes. For example, U.S. Pat. No. 2,814,601 to Currie et al., Nov. 26, 1957, which is hereby incorporated by reference, discloses that MQ resins can be prepared by converting a water-soluble silicate into a silicic acid monomer or silicic acid oligomer using an acid. When adequate polymerization has been achieved, the resin is end-capped with trimethylchlorosilane to yield the MQ resin. Another method for preparing MQ resins is disclosed in U.S. Pat. No. 2,857,356 to Goodwin, Oct. 21, 1958, which is hereby incorporated by reference. Goodwin discloses a method for the preparation of an MQ resin by the cohydrolysis of a mixture of an alkyl silicate and a hydrolyzable trialkylsilane organopolysiloxane with water. MQ resins have also reportedly been prepared by cohydrolysis of the corresponding silanes or by silica hydrosol capping methods known in the art. MQ resins used may also be prepared by the silica hydrosol capping processes of Daudt, et al., U.S. Pat. No. 2,676,182;

Another optional ingredient is a filler. The filler may be added in an amount up to 60 weight parts based on 100 weight parts of the silicone ionomer. Alternatively, from 0 to 50 weight parts based on 100 weight parts of the silicone ionomer may be used. Alternatively, from 5 to 30 weight parts on the same basis may be used. Fillers useful in the instant invention may be exemplified by, but not limited to, inorganic materials such as pyrogenic silica, precipitated silica and diatomaceous silica, ground quartz, aluminum silicates, mixed aluminum and magnesium silicates, zirconium silicate, mica powder, calcium carbonate, glass powder and fibers, titanium oxides of the pyrogenic oxide and rutile type, barium zirconate, barium sulphate, barium metaborate, boron nitride, lithopone, the oxides of iron, zinc, chrome, zirconium, and magnesium, the different forms of alumina (hydrated or anhydrous), graphite, lamp black, asbestos, and calcined clay and organic materials such as the phthalocyamines, cork powder, sawdust, synthetic fibers and synthetic polymers (polytetrafluoroethylene, polyethylene, polypropylene, polystyrene and polyvinyl chloride). The filler may be of a single type or mixtures of several types.

In general, small amounts of additional ingredients may also be added to the compositions of this invention. For example, antioxidants, pigments, stabilizers, moisture scavengers, diluents, carriers, and others, may be added as long as they do not materially alter the requirements stipulated herein.

The flow temperature corresponds to the temperature at which the material has the ability to conform to any shape. Modifying the flow temperature is useful both for processing the material and for applications like hot melt. Generally, the flow temperature determines the minimum temperature needed to process the material and at the same time the maximum temperature of use before the formed shape loses its integrity.

The silicone ionomers useful to make the thermoplastic elastomers of the invention can be made by hydrosilylating a siloxane polymer bearing hydrogen groups (SiH functionality) with protected undecylenic acid (e.g. trimethylsilylated undecylenic acid) in solution. A platinum catalyst may be used to aid the reaction. After stripping the polymer from solvent, the siloxane polymer bearing protected undecylenic acid groups is converted into the carboxylic acid functional derivatized material by deprotection with methanol. To obtain the corresponding ionomeric silicones, the carboxylic acid functional siloxane is neutralized with metal salts, usually metal acetylacetonates, being mindful of the valency of the specific metal counter-ion of interest. For example, for a divalent counter-ion, a molar ratio of 1 to 2 metal salt to carboxylic acid should be used to attain 100% neutralization. After formation of the ionomeric siloxane, the solvent is stripped under vacuum to obtain a solid material with thermoplastic elastomeric properties. Optional ingredients can be added before the stripping step or afterwards by using an appropriate co-solvent. Alternatively, extrusion at temperatures above the flow temperature of the ionomeric siloxane can be used to introduce optional ingredients without the use of solvent.

To prepare or recycle a finished part or to seal or bond two substrates, the silicone ionomer needs to be heated above its flow temperature, which will be specific to the molecular weight, ion content, type of counter-ion and extent of neutralization of the silicone ionomer. The strength of the physical cross-links introduced through the ionic aggregates can be modified by changing the metal counter-ion type. For example changing the metal counter-ion from $Na^+$ to $Mg^{++}$ will increase the flow temperature. In addition, increasing the metal ion neutralization extent increases the strength of the physical crosslinks and therefore also increases the flow temperature. In this way, flow temperatures can be adjusted.

Precursor linear polydimethylsiloxanes (PDMS) are typically flowable liquids at temperatures as low as −80° C. Conversion to a metal neutralized silicone ionomer can increase the flow temperature dramatically, for example for the linear polydimethylsiloxanes from −80° C. to 300° C. Depending on the molecular weight, ion content, type of counter-ion and extent of neutralization, the flow temperature of a silicone ionomer can be at least 0° C. Alternatively, the flow temperature of a silicone ionomer can range from 0° C. to 300° C., alternatively from 100° C. to 300° C., alternatively from 100° C. to 250° C.

The storage moduli of silicone ionomers at room temperature are from $10^2$ Pa to $10^8$ Pa, alternatively from $10^3$ Pa to $10^8$ Pa, alternatively from $10^4$ to $10^7$ Pa. As a reference, a typical high molecular weight polydimethylsiloxane (termed 'gum') will have a storage modulus in the $10^3$ to $10^4$ Pa range, considerably lower than what can be achieved with silicone ionomers. A glassy material, for example a polydimethylsiloxane at temperature below its glass transition (below −125° C.) has a storage modulus of $10^9$ Pa.

In addition to heat, one may use solvent to recycle the thermoplastic elastomers of the present invention. A combination of an aromatic hydrocarbon solvent like toluene, xylene and a polar alcohol like methanol, preferably in a 9/1 volume ratio should be used. The aromatic solvent ensures dissolution of the siloxane backbone, while the polar alcohol is needed to break the ionic aggregates and dissolve the silicone ionomer.

The thermoplastic elastomers of this invention find utility in many of the same applications as now being served by silicone pressure sensitive adhesives (PSAs) and/or organic or silicone hot melt adhesives, particularly in such thermoplastic industries as automotive, electronic, construction, space and medical. In addition, the thermoplastic elastomers may be used for personal care products, for example as a gellant.

When the thermoplastic elastomers of the present invention are used as hot melt PSAs, they may be applied to various substrates by techniques currently employed for dispensing other type of hot melt materials (e.g., hot melt gun, spraying, extrusion, spreading via heated draw-down bars, doctor blades or calendar rolls). The common factor in these methods is that the composition is heated to a temperature sufficient to induce flow before application. Upon cooling to ambient conditions, the compositions of the present invention range from tacky low modulus adhesives to non-tacky, non-slump PSAs which may be used to bond components or substrates to one another. Bonding is imparted not only through the transition from a flowable mass to a rubbery elastomer but can also take place through strong ionomer—substrate interactions such as ionomer—silanol interactions in case of glass substrates. The silicone ionomers deliver green strength by passing through the ionomer transition upon cooling, so sealed structures can be immediately handled without risking the integrity of the seal or bond.

Unlike other PSAs or hot melts, after the desired components are bonded with the thermoplastic elastomer of the invention, the present invention only requires that the temperature cool down for it to harden, there is no curing time. Rather, upon cooling, the ionic aggregate re-form to an elastomer. With other PSAs or hot melts, the time required for completion of the cure process ranges from about a day to more than a month, depending for example, upon the catalyst type, catalyst level, temperature and humidity.

Another embodiment of the present invention is a method of sealing or bonding at least two substrates comprising the steps of (i) heating at least one thermoplastic elastomer comprising at least one silicone ionomer so that it flows;

(ii) applying to a first substrate, the heated thermoplastic elastomer;

(iii) positioning a second substrate so the heated thermoplastic elastomer effects a seal therebetween or causes the first substrate to bond to the second substrate before the heated thermoplastic elastomer cools down;

(iv) allowing the heated thermoplastic elastomer to cool down.

The temperature to which the thermoplastic elastomer needs to be heated will vary depending on the type of cation, mole fraction of the cation and the extent of neutralization present, however, it is necessary that the temperature be high enough so the thermoplastic elastomer flows. Any substrate may be used including glass, aluminum, steel, etc.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All parts and percentages in the examples are on a weight basis and all measurements were obtained at 25° C., unless indicated to the contrary.

Test Methods:

$^{29}$Si Nuclear Magnetic Resonance Spectroscopy (NMR)

Ionomer samples for NMR analysis were prepared by introducing approximately 4 grams of sample into a vial and diluting with approximately 4 grams of 0.04M Cr(acac)3 solution in CDCl3. Samples were mixed and transferred into a silicon-free NMR tube. Spectra were acquired using a Varian Mercury 400 MHz NMR.

Rheology Measurements (Storage Modulus, Loss Modulus, Viscosity Measurements):

A TA Instruments ARES-RDA (2KSTD standard flexural pivot spring transducer) with forced convection oven was used to measure the storage modulus (G') and loss modulus (G") of siloxane ionomers. Test specimens (typically 8 mm wide, 0.1 mm thick) were loaded in between parallel plates and measured using small strain oscillatory rheology while ramping the temperature in a range from −120° C. to 250° C. at 2° C./min (frequency 1 Hz). Viscosity of flowable liquids were measured using the same instrument in steady shear mode at different temperatures, typically using a 25 mm cone and plate fixture.

Gel Permeation Chromatography (GPC):

The sample was prepared in Toluene at 0.5% concentration, filtered and analyzed against PDMS standards using refractive index detection. The columns were two 300 mm Mixed C with a 50 mm guard column. The flow rate was 1 mL/min.

DSC Experiments

A TA Instruments Q2000 differential scanning calorimeter (DSC) with a liquid nitrogen cooling system (LNCS) was used to measure the glass transition ($T_g$). A sample of about 10 mg was introduced in a TA Instruments hermetic pan. Indium was used as a calibration standard for heat flow and temperature. Samples were heated at 10° C./min using helium as a purge gas (25 mL/min).

Tensile Properties

Stress-strain properties of ionomer siloxanes were obtained by testing dog bone shaped samples in an INSTRON at a 5 mm/min drawing speed. Samples were tested up to failure.

Example 1

Synthesis of Polydimethylsiloxanes (PDMS) Bearing 3.3 mol % Pendant Carboxy Acid Functional Radicals Reactants:

PDMS bearing pendant hydrogen groups (SiH) amounting to 3.3 mol % SiH, more specifically with composition: $(Me_3SiO_{1/2})_{0.017}(MeHSiO_{2/2})_{0.033}(Me_2SiO_{2/2})_{0.95}$ where Me is a methyl radical; degree of polymerization (d.p.) 200, steady shear viscosity at 25° C.: $\eta_{25}$=0.35 Pa·s; prepared by methods known in the art such as described in EP 0196169B1

Toluene (Fisher Scientific)

trimethylsilylated undecylenic acid, prepared as described, for example, in EP0196169B1

Pt on alumina (heterogeneous catalyst, Sigma Aldrich)

methanol (Sigma Aldrich)

319.4 g of a PDMS having pendant hydrogen groups (SiH functionality) amounting to 3.3 mol % SiH was loaded to the reaction vessel together with 319.4 g toluene to make a 50% solids solution. A nitrogen blanket was applied, the mixture was heated to 100° C. and 55 g of trimethylsilylated undecylenic acid was added. This amounted to a 50 mol % excess of the protected acid (1.5 mol protected acid for 1 mol SiH). 1.17 g of a 1 wt % Pt on alumina powder was added, corresponding to 20 ppm of Pt based on the sum of SiH functional PDMS, toluene and trimethylsilylated undecylenic acid. The mixture was heated and kept at 100° C. for 2.5 hours. Additional trimethylsilylated undecylenic acid (22.3 g) was introduced in two steps and the reaction temperature increased to 110° C. for 6 hours. Infrared analysis indicated complete conversion of the SiH functionality on PDMS. The reaction mixture was filtered through a 0.45 m filter. A colorless, clear material was obtained. The polymer was stripped from solvent and residual unreacted trimethylsilylated undecylenic acid using a 0.4 mm Hg vacuum at 140° C. To deprotect polymer and convert it to the carboxy acid functional version, 336 g of the polymer was added to 224 g of toluene (60 wt % solids solution). 50 g of methanol was added to deprotect the acid under reflux for two hours.

NMR analysis confirmed the expected final structure of the product based on the SiH PDMS precursor: $(Me_3SiO_{1/2})_{0.018}(MeR'SiO_{2/2})_{0.032}(Me_2SiO_{2/2})_{0.95}$ where Me is a methyl radical and R' corresponds to the carboxy acid functional radical -G-COOH with G corresponding to $—(CH_2)_{10}—$ (based on undecylenic acid).

The material was a clear, color-free, solvent-free low viscosity liquid. Molecular weight and viscosity data on this polymer: $M_w$=28,000 g/mol; $M_n$=8,810 g/mol; $\eta_{25}$=0.35 Pa·s

Example 1

Synthesis of Polydimethylsiloxanes Bearing Pendant Carboxy Acid Functional Radicals, Neutralized with Different Levels of Lithium Counter-Ions The carboxy acid functional PDMS, prepared in example 1, was neutralized with Lithium counter-ions (Li$^+$) to three different extents: 50%, 75% and 100%. In the case of 50%, for example, half of the carboxy acid functional radicals are converted with the Li$^+$ counter-ion to give $—(CH_2)_{10}—COO^-Li^+$ and half are not converted and remain $—(CH_2)_{10}—COOH$. Each polymer was neutralized by loading 30 g of the carboxy acid functional PDMS with the desired amount of lithium acetylacetonate (Sigma Aldrich) to reach the stated levels of neutralization and 10 g of methanol and 20 g of toluene. After mixing for 1 hour at 70° C., the temperature was increased to 150° C. and vacuum was applied at 15 mbar for 2 hours to ensure the by-product of neutralization, acetylacetone, was removed while driving the neutralization to completion. The following materials were obtained. $(Me_3SiO_{1/2})_{0.018}(MeR'SiO_{2/2})_x(MeR''SiO_{2/2})_y(Me_2SiO_{2/2})_{0.95}$, with R'—$(CH_2)_{10}$COOH and R''—$(CH_2)_{10}$—COO$^-$Li$^+$

TABLE 1

Characteristics of Li$^+$ neutralized carboxy acid functional PDMS: $(Me_3SiO_{1/2})_{0.018}(MeR'SiO_{2/2})_x(MeR''SiO_{2/2})_y(Me_2SiO_{2/2})_{0.95}$ with R'—$(CH_2)_{10}$COOH and R''—$(CH_2)_{10}$COO$^-$Li$^+$

| Targeted neutralization | Composition (NMR) | Observation at 25° C. | Viscosity at 25° C. |
|---|---|---|---|
| 0% | x = 0.032, y = 0 | clear, low viscosity liquid | 0.300 Pa·s |
| 50% | x = 0.016, y = 0.016 | clear, high viscosity liquid | 14.6 Pa·s |
| 75% | x = 0.008, y = 0.024 | clear, very high viscosity liquid | 22,000 Pa·s |
| 100% | x = 0, y = 0.032 | clear, elastic solid gel | $1.10^6$ Pa·s* |

*value estimated from an oscillatory rheology measurement using small strains

Example 3

Viscoelastic Behavior of Polydimethylsiloxanes Bearing Pendant Carboxy Acid Functional Radicals, Neutralized with Different Levels of Lithium Counter-Ions: Illustration of Thermoplastic Elastomeric Behavior and Control Over the Melt Flow Temperature and Rubbery Plateau Modulus Insight into the drastic viscoelastic property changes that take place when an acid-functional PDMS is neutralized to different extents with Li$^+$ can be obtained from small strain shear oscillatory rheology experiments, as shown in FIG. 1. Both the storage modulus (G') and loss modulus (G") are shown as a function of temperature are shown. The storage modulus relates to the rigidity or stiffness of the material, while the loss modulus is proportional to the amount of energy dissipated through heat. The acid-functional PDMS neutralized 100% with Li$^+$ counter-ions (curve with x=0, y=0.032), for example following its rheological profile from low to high temperature, is in the glassy state below the glass transition of the PDMS matrix (around −125° C.), passes through the glass/rubber transition to a rubbery material extending from −100° C. to room temperature, and enters the melt-flow regime into a viscous liquid beyond this temperature range. This curve indicates one of the key aspects of the current invention related to thermoplastic elastomers. The metal neutralized PDMS ionomers behave like elastomeric rubbers at temperature around room temperature, where energy can be stored and small time-scale deformations to the material are reversible. Once heated to higher temperatures, the thermal break-up of the ionomeric interactions reverts the material back to a viscous liquid. In this high temperature range, the material behaves like a high molecular weight PDMS polymer.

Reducing the level of neutralization is a convenient method to alter the flow temperature and the temperature range of the rubbery plateau modulus. Note that the G' value in the rubbery plateau regime or the rubbery plateau modulus is indicative for the cross-link density, which in case of these ionomeric siloxanes corresponds to the physical cross-links that form through ionomeric aggregates. This value will relate to application-related properties like hardness, tack and elasticity.

Example 4

Synthesis of Polydimethylsiloxanes Bearing Pendant Carboxy Acid Functional Radicals, 50% Neutralized with Different Metal Counter-Ions: Impact on Flow Temperature and Rubbery Plateau Modulus The carboxy acid functional PDMS, prepared in example 1, was neutralized with a range of metal counter-ions: metals like Al$^{3+}$ (Aluminum trivalent, using Aluminum acetylacetonate, Sigma Aldrich), transition metals like Zn$^{++}$ (Zinc divalent, using Zinc acetylacetonate, Sigma Aldrich), Mn$^{++}$ (Manganese divalent, using Manganese (II) acetylacetonate, Sigma Aldrich), Zr$^{4+}$ (Zirconium tetravalent, using Zirconium acetylacetonate, Sigma Aldrich), Mn$^{3+}$ (Manganese trivalent, using Manganese (III) acetylacetonate, Sigma Aldrich), Cr$^{3+}$ (Chromium trivalent, using Chromium acetylacetonate, Sigma Aldrich) and alkali metals like Li$^+$ (Lithium monovalent, using Lithium acetylacetonate, Sigma Aldrich, see Example 2). 50% conversion of the carboxy functional radical was targeted based on the valency of the counter-ion under investigation. For example, 50% neutralization with Cr$^{3+}$ corresponded to mixing 0.5/3 mol of the Chromium salt with 1 mol of the —$(CH_2)_{10}$—COOH functionality on PDMS. The procedure was the same for all metal counter-ions and consisted of loading 30 g of the carboxy acid functional PDMS with the desired amount of the metal acetylacetonate to reach the stated levels of neutralization and 10 g of methanol and 20 g of toluene. After mixing for 1 hour at 70° C., the temperature was increased to 150° C. and vacuum was applied at 15 mbar for 2 hours. This makes sure the by-product of neutralization, acetylacetone, is removed while driving the neutralization to completion. Materials were synthesized so that half of carboxy functional radicals remained with the other half neutralized with the appropriate metal counter-ion. Materials properties are given in Table 2.

TABLE 2

Characteristics of 50% neutralized carboxy acid functional PDMS based on $(Me_3SiO_{1/2})_{0.018}(MeR'SiO_{2/2})_{0.032}(Me_2SiO_{2/2})_{0.95}$ with R'—$(CH_2)_{10}$—COOH

| Counter-ion | Observation at 25° C. | Rubbery plateau modulus*, Pa |
|---|---|---|
| Li$^+$ | clear, high viscosity liquid | 45,400 |
| Cr$^{3+}$ | clear soft crumbly solid, green color | 6,919 |
| Al$^{3+}$ | clear, soft crumbly solid | 46,854 |
| Mn$^{2+}$ | clear, high viscosity liquid, brown color | 143,000 |
| Mn$^{3+}$ | clear, high viscosity liquid, dark brown color | 41,081 |
| Zn$^{2+}$ | clear, high viscosity liquid | 72,278 |
| Zr$^{4+}$ | clear, rubbery solid | 14,405 |
| mg$^{2+}$ | clear, rubbery solid | 278,000 |

*the rubbery plateau modulus determined as G' at the minimum in tan δ(G"/G') in a tan δ vs. temperature oscillatory shear rheology experiment As indicated in Table 2, a range of rubbery plateau moduli can be obtained by changing the metal counter-ion. Generally, a higher rubbery plateau modulus results in harder, less tacky materials.

Example 2

Synthesis of a Low Molecular Weight Polydimethylsiloxanes Bearing Telechelic Carboxy Acid Functional Radicals and its Li+ Neutralized Version To make the endcap or telechelic versions of ionomeric PDMS, the starting precursor needs to be an SiH terminated PDMS and the procedure outlined in example 1 and 2 can be used. The procedure used to make a 10 mol % telechelic carboxy acid functional PDMS consists of using the following reactants:

PDMS bearing telechelic hydrogen groups (SiH) amounting to 10 mol % SiH, more specifically DOW CORNING® Q2-5057S (Dow Corning, Midland, Mich.)
toluene (Fisher Scientific)
trimethylsilylated undecylenic acid, prepared as described, for example, in EP0196169B1
Pt on alumina (heterogeneous catalyst, Sigma Aldrich)
methanol (Sigma Aldrich)

150 g of a PDMS having telechelic hydrogen groups (SiH functionality) amounting to 10 mol % SiH was loaded to the reaction vessel together with 150 g toluene to make a 50% solids solution. A nitrogen blanket was applied, the mixture was heated to 90° C. and 60.53 g of trimethylsilylated undecylenic acid was added. This amounted to a 4 mol % excess of the protected acid (1.04 mol protected acid for 1 mol SiH). 0.72 g of a 1 wt % Pt on alumina powder was added, corresponding to 20 ppm of Pt based on the sum of SiH functional PDMS, toluene and trimethylsilylated undecylenic acid. The mixture was heated and kept at 100° C. for 1 hour. Infrared analysis indicated no residual SiH after this step. The reaction mixture was filtered through a 0.22 m filter. A colorless, clear material was obtained. The polymer was stripped from solvent and residual unreacted trimethylsilylated undecylenic acid using a 0.4 mm Hg vacuum at 140° C. To deprotect the polymer and convert it to the carboxy acid functional version, 150 g of the polymer was added to 100 g of toluene (60 wt°/0 solids solution). 100 g of methanol was added to deprotect the acid under reflux for two hours. The final material was stripped from solvent on a rotary evaporator at 150° C. and 0.8 mmHg for 1 hour.

NMR analysis confirmed the expected final structure of the product based on the SiH PDMS precursor: $(Me_2R'SiO_{1/2})_{0.103}(Me_2SiO_{2/2})_{0.897}$ where Me is a methyl radical and R' corresponds to the carboxy acid functional radical —$(CH_2)_{10}$—COOH. The material was a clear, color-free, solvent-free low viscosity liquid.

The Li+ 100% neutralized version of the 10.3 mol % carboxy acid functional PDMS material was obtained by loading 50 g of the PDMS precursor into 35 g toluene, 15 g methanol and adding 5.907 g Lithium acetylacetonate stoichiometrically. The reaction mixture was heated to 80° C. for 1 h. The polymer solution was stripped from solvent on a rotary evaporator at 155° C. and 0.8 mmHg for 2.5 h. The final material was a colorless, hard solid at room temperature.

Example 6

Synthesis of High Molecular Weight Polydimethylsiloxanes ($M_w$=100,000 g/mol) Bearing 1 Mol % Telechelic Carboxy Acid Functional Radicals, 100% Neutralized With Mg++Counter-Ions or 100% Neutralized with Li+ Counter-Ions The telechelic version of ionomeric PDMS with high molecular weight and consequently low carboxy acid functionality started from the SiH terminated precursor and follows a procedure similar to example 5. The procedure used to make a 1 mol % telechelic carboxy acid functional PDMS used the following reactants:

PDMS bearing telechelic hydrogen groups (SiH) amounting to 1.3 mol % SiH, more specifically with composition: $(Me_2HSiO_{1/2})_{0.013}(Me_2SiO_{2/2})_{0.987}$ where Me is a methyl radical; degree of polymerization (d.p.) is about 1,000 (see example 1 for specifics on SiH precursors);
toluene (Fisher Scientific)
trimethylsilylated undecylenic acid, prepared as described, for example, in EP0196169B1
Pt on alumina (heterogeneous catalyst, Sigma Aldrich)
methanol (Sigma Aldrich)

175 g of a PDMS having telechelic hydrogen groups (SiH functionality) amounting to 1.3 mol % SiH was loaded to the reaction vessel together with 61 g toluene to make a 74% solids solution. A nitrogen blanket was applied, the mixture was heated to 100° C. and 8.27 g of trimethylsilylated undecylenic acid was added. This amounts to a 5 mol % excess of the protected acid (1.05 mol protected acid for 1 mol SiH). 0.49 g of a 1 wt % Pt on alumina powder was added, corresponding to 20 ppm of Pt based on the sum of SiH functional PDMS, toluene and trimethylsilylated undecylenic acid. The mixture was heated and kept at 100° C. for 1 hour. Infrared analysis indicated very little residual SiH after this step. The reaction mixture was filtered through a 0.22 m filter. A colorless, clear material was obtained. To deprotect the polymer and convert it to the carboxy acid functional version, 40 g of methanol was added. The mixture was heated at reflux for 2 hours. The final material was stripped from solvent on a rotary evaporator at 150° C. and 0.8 mmHg for 1 hour.

NMR analysis confirmed the expected final structure of the product based on the SiH PDMS precursor: $(Me_2R'SiO_{1/2})_{0.013}(Me_2SiO_{2/2})_{0.987}$ where Me is a methyl radical and R' corresponds to the carboxy acid functional radical —$(CH_2)_{10}$—COOH. The material was a clear, color-free, solvent-free low viscosity liquid.

The Li+ 100% neutralized version of the 1.3 mol % carboxy acid functional PDMS material was obtained by loading 50 g of the PDMS precursor into 35 g toluene, 15 g methanol and adding 0.833 g Lithium acetylacetonate stoichiometrically. The reaction mixture was heated at 80° C. for 1 hour. The polymer solution was stripped from solvent on a rotary evaporator at 170° C. and 0.6 mmHg for 2 hours. The final material was a colorless, extremely high viscosity liquid at room temperature.

The Mg++ 100% neutralized version of the 1.3 mol % carboxy acid functional PDMS was made similarly by adding magnesium acetylacetonate (Sigma Aldrich) stoichiometrically to the carboxy acid precursor.

A comparison between the low molecular weight/high ion containing Li+ neutralized ionomer from Example 5 and the high molecular weight/low ion containing Li+ neutralized ionomer from Example 6 is given in Table 3. It is clear from this analysis that the ion content dominates the rheology behavior, since the highest rubbery plateau modulus and flow temperature is found for the 10 mol % ionomer, which has the lowest molecular weight. From a rheological perspective, the highest ion containing polymer self-assembles into a much higher effective molecular weight or cross-link density than its low ion counter-part. When compared to the results in Example 4 on the effect of counter-ion type, the telechelic ionomers based on one counter-ion type but different ion contents can have some advantages if material properties at room temperature (rubbery plateau modulus) and flow temperatures need to be optimized, for example, for a hot melt application, without changing the metal counter-ion used. Basically, these two procedures to alter the properties of PDMS-based ionomers offer flexibility in materials design.

TABLE 3

Characteristics of 100% Li⁺ neutralized telechelic carboxy acid functional PDMS: high $M_w$/low ion content (1.3 mol %, Example 6) and low $M_w$/high ion content (10 mol %, Example 5)

| Ion content (—$(CH_2)_{10}$—COO⁻Li⁺) | Observation at 25° C. | Rubbery plateau modulus*, Pa | Flow temperature**, ° C. |
|---|---|---|---|
| 1.3 mol % | clear, extremely high viscosity | 217,000 | 120 |
| 10 mol % | clear, hard solid | 9,380,000 | 160 |

*rubbery plateau modulus determined as G' at the minimum in tan δ (G"/G') in a tan δ vs. temperature oscillatory shear rheology experiment
**flow temperature, as determined from the temperature at which G' reaches 1 kPa upon heating Example 7

Comparison Between a High Molecular Weight Polydimethylsiloxanes ($M_w$=100,000 g/mol) Bearing 1 Mol % Carboxy Acid Functional Radicals, 100% Neutralized with Mg⁺⁺ Counter-Ions and a Chemically Cross-Linked PDMS Rubber A comparison is made between an ionomeric PDMS with physical cross-links and a chemically cross-linked PDMS rubber as far as rheology and mechanical properties. To compare these systems side-by-side, a similar cross-link density is targeted for both materials. This was achieved by selecting the vinyl-functional PDMS and SiH cross-linker for the chemically cross-linked PDMS rubber appropriately. To check the level of cross-link density, either physical or chemical, the rubbery plateau modulus was used, since this value can be used to calculate the molecular weight between cross-links, $M_C$, regardless of the chemistry used:

$$M_C = \rho . R . T / G^N_0$$

with: $M_C$ the molecular weight between cross-links, ρ the density, R the gas constant, T the temperature and $G^N_0$ the rubbery plateau modulus. The following two materials were compared in this manner:
1. 100% Mg⁺⁺ neutralized 1 mol % carboxy acid functional PDMS from example 7.
2. vinyl-functional PDMS cured with an SiH cross-linker using a Pt catalyst, based on the following formulation: 170 g DOW CORNING® SFD-117 Filtered Fluid (Dow Corning, Midland Mich.) a vinyl-containing polymer (d.p. 434), 30 g DOW CORNING® 2-7220 INTERMEDIATE a SiH cross-linker (Dow Corning, Midland Mich.), and 20 ppm of a Pt catalyst DOW CORNING® 2-0707 INT (PLATINUM 4) (Dow Corning, Midland Mich.) (0.56% Pt) was used in combination with 0.5 wt % of 2-methyl-3-butyn-2-ol inhibitor (Sigma Aldrich) to cure the rubber at 50° C. over 24 hours. The polymer, cross-linker and inhibitor were mixed together at room temperature and introduced in a vacuum oven at room temperature to get the bubbles out. The Pt catalyst was added to this mixture and the sample was introduced in an air evacuated oven at 50° C. for 2 days to fully cure the elastomer.
The rubbery plateau modulus values are similar for both materials as summarized in Table 4. The effective cross-link density of both materials must therefore be similar in a temperature range below 150° C. where the ionomer starts to flow. Note that the chemically cross-linked PDMS rubber doesn't exhibit flow at any temperature below its degradation temperature.

TABLE 4

Characteristics of 1. PDMS ionomer: 100% Mg⁺⁺ neutralized telechelic carboxy acid functional PDMS: high $M_w$/low ion content (1.3 mol %, Example 6) compared to 2. PDMS rubber: a chemically cross-linked PDMS rubber

| Material | Observation at 25° C. | Rubbery plateau modulus*, Pa | Flow temperature**, ° C. |
|---|---|---|---|
| PDMS ionomer | clear, elastic solid | 133,000 | 150 |
| PDMS rubber | clear, elastic solid | 190,000 | n/a*** |

Figure 2:
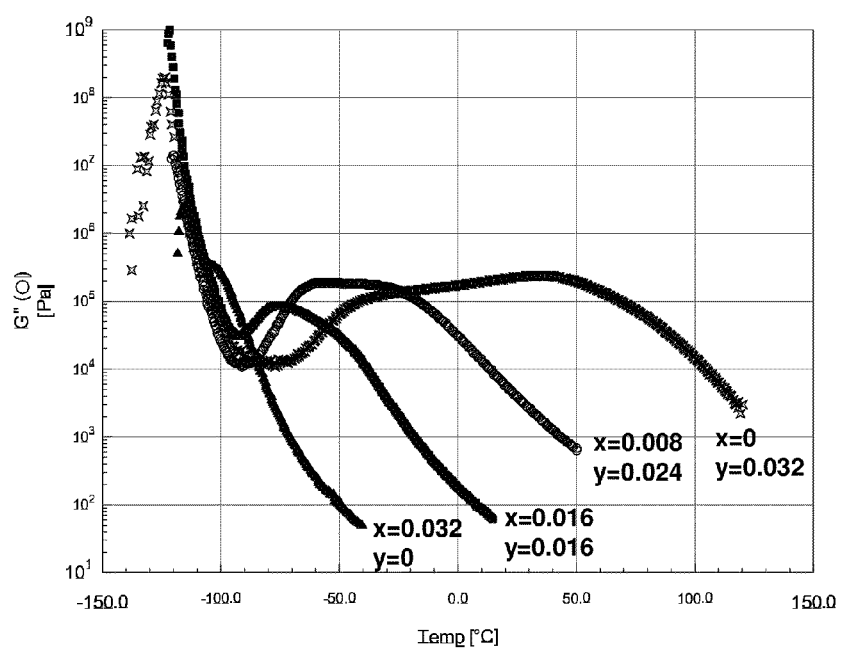
FIG. 2: Loss modulus (G'') of polydimethylsiloxanes bearing pendant carboxy acid functional radicals, neutralized with different levels of Lithium counter-ions; x and y refer to the Formula $(Me_3SiO_{1/2})_{0.018}(MeR'SiO_{2/2})_x(MeR''SiO_{2/2})_y(Me_2SiO_{2/2})_{0.95}$ with R'—$(CH_2)_{10}$—COOH and R''—$(CH_2)_{10}$—COO⁻Li⁺; measurements were performed under oscillatory shear using small sinusoidal strain (<5%).
Figure 3:
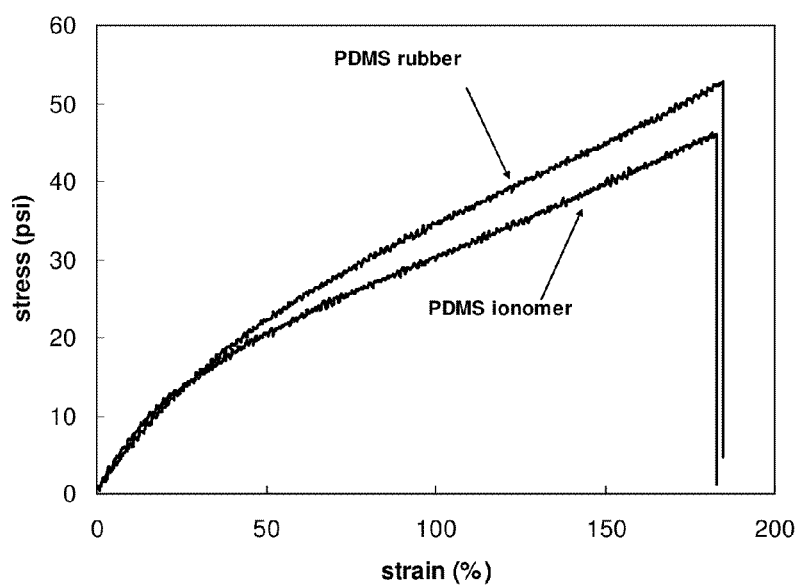
FIG. 3: Tensile properties at 25° C. measured at 2 inch/min strain speed comparing the PDMS ionomer and rubber from Example 7.

*rubbery plateau modulus determined as G' at the minimum in tan δ (G"/G') in a tan δ vs. temperature oscillatory shear rheology experiment
**flow temperature, as determined from the temperature at which G' reaches 1 kPa upon heating
***chemically cross-linked elastomeric rubber does not flow at any temperature To confirm the similarity in mechanical properties between the PDMS rubber and its ionomeric counterpart, FIG. 2 compares the tensile properties at room temperature. Both the tensile strength (around 50 psi=350 kPa) and strain at break (around 180%) are similar.

Example 8

Blends of PDMS Ionomers with Different Ion Contents

Two PDMS ionomers were blended to illustrate the level of property control that can be achieved by modifying the physical cross-link density. Two benefits are obtained simultaneously which are difficult to achieve with a chemically cross-linked PDMS:
1) The PDMS ionomers form miscible, transparent blends over a wide composition range. This is in part due to their identical chemical constituents, even though the ion content might differ.
2) There is no issue with stoichiometric imbalance since the physical cross-link points are formed from the aggregation of one type of functionality, e.g. COO⁻Li⁺. This is in contrast to a vinyl/SiH cured PDMS, for example, where higher cross-link densities would require both the vinyl and SiH content to be increased if no stoichiometric imbalance is acceptable.

A telechelic PDMS ionomer with high ion content, detailed in example 5 (10 mol % COO⁻Li⁺ PDMS ionomer), was blended with a pendant PDMS ionomer with low ion content (1.9 mol % COO⁻Li⁺ ionomer) similar to the one detailed in Example 2. Although the inventors do not want to be held to one theory, it is believed, that the low ion content, high molecular weight PDMS ionomer with low ion content forms the bulk of the material and introduces some entanglement strength to the blends' properties. The low molecular weight, high ion content PDMS ionomer can be considered to be a physical cross-linker, linking sites of the high molecular weight ionomer through ionic aggregates.

The blending procedure consisted of introducing the appropriate amounts of each ionomer into a 9/1 mixture of toluene to methanol to make a 20% solids solution. A rotating mixing wheel was used for 10 hours to ensure complete dissolution. Mixtures were introduced on Teflon films and heat treated using the following step-wise profile: 1 hour at 80° C., 1 hour at 100° C., 20 min at 150° C. Samples were allowed to cool to room temperature slowly. Table 5 contains the details on the effect of blend ratio on rheological properties. All the samples were transparent solid films at room temperature. The table shows that a range of rubbery plateau moduli and flow temperatures can be accessed simply by blending two PDMS ionomers. This adds materials design flexibility since only two materials have to be synthesized while a blend can be made to reach a certain targeted behavior.

TABLE 5

Characteristics of ionomer blends based on A) a 100% $Li^+$ neutralized telechelic carboxy acid functional PDMS: low $M_w$/high ion content (10 mol %, example 5) and B) a 100% neutralized pendant carboxy acid functional PDMS: high $M_w$/low ion content (1.9 mol %, similar to Example 2)

| Ratio A/B | Observation at 25° C. | Rubbery plateau modulus*, Pa | Flow temperature**, ° C. |
|---|---|---|---|
| 1/0 | clear, hard solid, non-tacky | 9,380,000 | 160 |
| 3/7 | clear, rubbery solid, slight tack | 4,220,000 | 158 |
| 2/8 | clear, rubbery solid, slight tack | 2,980,000 | 154 |
| 1/9 | clear, rubbery solid, slight tack | 2,000,000 | 146 |
| 0/1 | clear, flexible, tacky solid | 1,000,000 | 137 |

*rubbery plateau modulus determined as G' at the minimum in tan δ (G"/G') in a tan δ vs. temperature oscillatory shear rheology experiment
**flow temperature, as determined from the temperature at which G' reaches 1 kPa upon heating Example 9

Synthesis of Resin-Linear Materials

An additional level of control over material properties and compatibility can be achieved by modifying the base siloxane, either by incorporating branching or introducing phenyl modification. Branching will dramatically raise the glass transition of the siloxane polymer, which is around −125° C. for PDMS-based ionomers. Phenyl modification will also raise the glass transition but, more importantly, improve compatibility with organic matrices like epoxides, polyesters, acrylates, etc. . . . A phenyl-modified, branched siloxane ionomer with the following composition was targeted: $(MeR'SiO_{2/2})_{0.09}(MeR''SiO_{2/2})_{0.81}(R''SiO_{3/2})_{0.10}$ with R'—$(CH_2)_{10}$—COOH and R" a phenyl radical.

A different procedure was used in this case, even though hydrosilylation with trimethylsilylated undecylenic acid could also be employed in this case. More information on the procedure which starts from an amine-functional precursor and uses itaconic acid to convert into a carboxy-functional material, can be found in Berger A.; Fost D. L. U.S. Pat. No. 5,596,061; 1997, Organosilicone having a carboxyl functional group thereon. Hydrolysis and condensation of the following alkoxysilanes will result in the targeted building blocks:

phenylmethyldimethoxy silane (DOW CORNING® Z-2588 Phenylmethyldimethoxy Silane) 597.9 g (3.28 mol)
aminopropyl methyl diethoxysilane (DOW CORNING® Z-6015 Silane) 61.2 g (0.32 mol)
phenyltrimethoxysilane (DOW CORNING® Z-6124 Silane) 79.3 g (0.4 mol)

Other reactants/catalysts that were used:
xylenes (Sigma Aldrich)
de-ionized water
potassium hydroxide (1 N KOH aq, Sigma Aldrich)
hydrochloric acid (1 N HCl aq, Sigma Aldrich)
itaconic acid (Sigma Aldrich)

A reaction vessel was loaded with the alkoxysilanes and heated to 50° C. 9.56 mL of 1N KOH was added followed by 151.4 g of de-ionized water (amounts to twice the stoichiometric amount). The temperature was raised to 73° C. for 30 min. 536 g of xylenes were added. The volatiles were distilled off up to a reaction temperature of 85° C. The aqueous phase was removed and the reaction mixture was cooled to 50° C. 9.56 mL of 1N HCl was added to neutralize the KOH and stirring was applied for 1 h at 25° C. The mixture was heated to reflux and water was removed by azeotropic distillation. After cooling the reaction mixture to 85° C., 44.05 g itaconic acid was added, which corresponds to a 5 mol % excess to the amine (—$NH_2$) groups. The reaction mixture was heated to reflux for 3 hours and water was again removed using azeotropic distillation. The final product was stripped from solvent on a rotary evaporator at 150° C. using 0.5 mmHg vacuum for 1 h. The product was a solvent-free, clear, orange-color viscous liquid at room temperature. The composition of the final material as confirmed by NMR:$(MeR'SiO_{2/2})_{0.093}$ $(MeR''SiO_{2/2})_{0.799}(R''SiO_{3/2})_{0.10}$ with R'—$(CH_2)_{10}$—COOH and R" a phenyl radical To prepare the metal neutralized versions of the carboxy-functional branched phenyl siloxane ionomer, the polymer was dissolved in a 6/4 toluene/methanol mixture at 40 wt % polymer solids. The appropriate metal acetylacetonate was introduced at the targeted stoichiometry and the reaction mixture was heated to 85° C. for 1 hour with mixing. The metal neutralized carboxy-functional siloxane was stripped from solvent on a rotary evaporator at 160° C. and 0.6 mmHg vacuum for 1 hour.

A range of metal counter-ions were used to prepare 100% neutralized versions of the carboxy-functional branched phenyl siloxane ionomer, resulting in the properties listed in Table 6.

TABLE 6

Characteristics of metal neutralized branched phenyl siloxane ionomers based on $(MeR'SiO_{2/2})_{0.093}(MeR''SiO_{2/2})_{0.799}(R''SiO_{3/2})_{0.10}$ with R'—$(CH_2)_{10}$—COOH and R" a phenyl radical

| Counter-ion | Observation at 25° C. | Rubbery plateau modulus*, Pa | Flow temperature**, ° C. | Glass transition***, ° C. |
|---|---|---|---|---|
| $Zn^{2+}$ | clear, tacky solid, flows over time | n.a. | 41 | 0 |
| $Na^+$ | clear, tacky solid, some elasticity | 417,000 | 55 | −2 |
| $Li^+$ | clear, tacky solid, doesn't flow | 327,000 | 81 | −3 |
| $Mg^{2+}$ | clear, slightly tacky | 5,380,000 | 142 | −2 |
| $Ca^{2+}$ | clear, tacky solid | 4,000,000 | 160 | −1 |
| $Cu^{2+}$ | clear, crumbly solid, elastic | 2,590,000 | 155 | 0 |
| $Ni^{2+}$ | clear, crumbly solid | 1,560,000 | 200 | 2 |

*rubbery plateau modulus determined as G' at the minimum in tan δ (G"/G') in a tan δ vs. temperature oscillatory shear rheology experiment
**flow temperature, as determined from the temperature at which G' reaches 1 kPa upon heating
***glass transition as measured by oscillatory shear rheology as the maximum in tan δ vs. temperature The results in Table 6 indicate the wide range of properties that are accessible starting from the same carboxy-functional precursor. These materials are prime candidates for hot melt applications that can rely both on the increased matrix glass transition (around 0° C. in Table 6) and the selection of counter-ion to meet certain melt flow specifications (melt flow temperatures from 41° C. up to 200° C. in Table 6). The tensile properties listed in Table 7 indicate that these materials also hold promise as elastomeric rubbers.

TABLE 7

Tensile properties of a Li$^+$ and Mg$^{2+}$ neutralized branched phenyl siloxane ionomer based on (MeR'SiO$_{2/2}$)$_{0.093}$(MeR"SiO$_{2/2}$)$_{0.799}$(R"SiO$_{3/2}$)0.10 with R' —(CH$_2$)$_{10}$—COOH and R" a phenyl radical

| Counter-ion | Tensile strength, MPa | Strain at break, % |
|---|---|---|
| Li$^+$ | 1.65 | 48 |
| Mg$^{2+}$ | 25 | 12 |

Example 10

Blends of PDMS Ionomers with MQ Resins as Hot Melt Materials

PDMS-based ionomers can be mixed with trimethylated silica particles (in short MQ resins) to obtain miscible blends with modified rheological behavior. In particular, the addition of MQ resin raises the glass transition and lowers the rubbery plateau modulus. The difference with the procedure used in Example 9 is that the MQ/PDMS ionomer blends do not rely on branching or phenyl incorporation to attain higher matrix glass transitions. In contrast, the presence of nano-scale MQ particles alters the PDMS polymer dynamics. As an example, a 50% Al$^{3+}$ neutralized PDMS ionomer (based on (Me$_3$SiO$_{1/2}$)$_{0.018}$(MeR'SiO$_{2/2}$)$_{0.032}$(Me$_2$SiO$_{2/2}$)$_{0.95}$ with R'—(CH$_2$)$_{10}$—COOH see Example 4) was used as the host polymer, modified with different levels of MQ resin (DOW CORNING® 5-7104 INT). A 50% solids solution was made of the ionomer and MQ resin in toluene/methanol (99/1 wt/wt) as a solvent. After mixing overnight, thin films were cast and stripped of solvent at 150° C. for 1 h and 180° C. for 30 min. All blends were transparent solids at room temperature. This indicates that MQ is fully miscible with the 50% Al$^{3+}$ neutralized PDMS ionomer in the composition range tested. Results are shown in Table 8.

TABLE 8

Characteristics of 50% Al$^{3+}$ neutralized PDMS ionomers blended in different ratios with MQ resin

| ionomer/MQ (wt/wt) | Rubbery plateau modulus*, Pa | Flow temperature**, ° C. | Glass transition***, ° C. |
|---|---|---|---|
| 1/0 | 45,384 | 109 | −116 |
| 7/3 | 27,350 | 108 | −94 |
| 6/4 | 18,600 | 77 | −70 |
| 5/5 | n.a.**** | 78 | −63 |
| 4/6 | n.a.**** | 120 | n.a. |

*rubbery plateau modulus determined as G' at the minimum in tan δ (G"/G') in a tan δ vs. temperature oscillatory shear rheology experiment
**flow temperature, as determined from the temperature at which G' reaches 1 kPa upon heating
***glass transition as measured by oscillatory shear rheology as the maximum in tan δ vs. temperature
****the rheological profile doesn't exhibit a rubbery plateau modulus due to the proximity of the flow temperature to the glass transition The advantage of using MQ resin as opposed to branching and phenyl incorporation for a hot melt application would be that MQ/PDMS blends are already used in this application and a lot of the beneficial properties of MQ/PDMS blends would be retained with the added control introduced by the ionomeric aggregates regarding faster solidification upon cooling and control over melt flow temperature. Therefore, PDMS ionomer could extend the application window of hot melt materials.

Example 11

PDMS Ionomers for Use in Gellants for Cosmetic Applications

The purpose of this evaluation was to use siloxane ionomers as transparent thickeners for cosmetic applications. An example would be a stick antiperspirant containing a large (75%) amount of carrier fluid. The 10 mol % Li$^+$ neutralized siloxane ionomer from example 4 was used. Before stripping the solvent after synthesis of the metal neutralized ionomer, a cosmetic carrier with high boiling point was added and the original solvent was removed by a solvent exchange procedure. Cyclosiloxanes were used as the carrier (DOW CORNING® 246 Fluid), for example, and a 1 hour stripping step at 100° C., 100 mmHg was sufficient to remove the original solvent (toluene) and retain the carrier. In this way, the 10 mol % Li$^+$ neutralized siloxane ionomer was swollen by the cyclosiloxanes to form a homogeneous, soft, clear gel.

That which is claimed is:

1. A thermoplastic elastomer comprising at least one silicone ionomer having an average Formula (1) (X$_v$R$_{3-v}$SiO$_{1/2}$)$_a$(X$_w$R$_{2-w}$SiO$_{2/2}$)$_b$(X$_y$R$_{1-y}$SiO$_{3/2}$)$_c$(SiO$_{4/2}$)$_d$ where each R is an independently selected monovalent alkyl group or aryl group, each X is independently selected from a monovalent alkyl group, aryl group and a carboxy functional group having a Formula (2) -G-COOZ, where G is a divalent spacer group having at least 2 spacing atoms, each Z is independently selected from hydrogen or a cation independently selected from alkali metal cations, alkali earth metal cations, transition metal cations, and metal cations, v is 0 to 3, w is 0 to 2, y is 0 to 1, 0≤a≤0.9; 0≤b<1; 0≤c<0.9, 0≤d<0.3 and a+b+c+d=1, provided that on average there is at least 0.002 mole carboxy functional groups per silicon atom and at least 10 mole percent of the Z groups of the carboxy functional group are an independently selected cation.

2. The thermoplastic elastomer of claim 1 where at least 50 mole percent of the Z groups of the carboxy functional group are an independently selected cation.

3. The thermoplastic elastomer of claim 1 where at least 75 mole percent of the Z groups of the carboxy functional group are an independently selected cation.

4. The thermoplastic elastomer of claim 1 where 100 mole percent of the Z groups of the carboxy functional group are an independently selected cation.

5. The thermoplastic elastomer of claim 1 where the cation is selected from a group consisting of Li, Na, K, Cs, Mg, Ca, Ba, Zn, Cu, Ni, Ga, Al, Mn, and Cr.

6. The thermoplastic elastomer claim 1 where the cation is selected from the group consisting of Li, Na, K, Zn, Ni, Al, Mn, and Mg.

7. The thermoplastic elastomer of claim 1 where on average there are at least 0.01 mole carboxy functional groups per silicon atom.

8. The thermoplastic elastomer of claim 1 where on average there are at least 0.02 mole carboxy functional groups per silicon atom.

9. The thermoplastic elastomer of claim 1 where on average there are from 0.002 to 0.5 mole carboxy functional groups per silicon atom.

10. The thermoplastic elastomer of claim 1 comprising a blend of at least two silicone ionomers.

11. The thermoplastic elastomer of claim 1 further comprising an MQ resin.

12. The thermoplastic elastomer of claim 1 further comprising filler.

* * * * *